United States Patent
Kennedy, II et al.

(10) Patent No.: US 7,993,411 B2
(45) Date of Patent: Aug. 9, 2011

(54) MEDICAL IMPLANT HAVING IMPROVED DRUG ELUTING FEATURES

(75) Inventors: Kenneth C. Kennedy, II, Clemmons, NC (US); Wenfeng Lu, Pfafftown, NC (US); Brian K. Rucker, King, NC (US); Vihar C. Surti, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 327 days.

(21) Appl. No.: 12/200,971

(22) Filed: Aug. 29, 2008

(65) Prior Publication Data
US 2009/0216319 A1    Aug. 27, 2009

Related U.S. Application Data

(60) Provisional application No. 60/969,358, filed on Aug. 31, 2007.

(51) Int. Cl.
*A61F 2/06* (2006.01)
*A61K 9/22* (2006.01)

(52) U.S. Cl. .............. 623/23.7; 623/1.44; 604/8

(58) Field of Classification Search ...... 623/23.64–23.7, 623/1.42–1.48; 604/8
See application file for complete search history.

(56) References Cited

U.S. PATENT DOCUMENTS

| | | |
|---|---|---|
| 4,917,686 A | 4/1990 | Bayston et al. |
| 5,217,493 A | 6/1993 | Raad et al. |
| 5,512,055 A | 4/1996 | Domb et al. |
| 5,599,321 A | 2/1997 | Conway et al. |
| 6,302,917 B1 | 10/2001 | Dua et al. |
| 6,872,225 B1 | 3/2005 | Rowan et al. |
| 7,118,600 B2 * | 10/2006 | Dua et al. ............. 623/23.68 |
| 2004/0249441 A1 * | 12/2004 | Miller et al. ............ 623/1.15 |
| 2005/0008763 A1 | 1/2005 | Schachter |
| 2008/0071355 A1 * | 3/2008 | Weber et al. ............ 623/1.16 |
| 2008/0086214 A1 * | 4/2008 | Hardin et al. .......... 623/23.7 |
| 2008/0234659 A1 * | 9/2008 | Cheng et al. ............ 604/523 |
| 2009/0281635 A1 * | 11/2009 | Li et al. ................ 623/23.66 |
| 2009/0285975 A1 * | 11/2009 | Bates et al. ............. 427/2.25 |
| 2010/0021523 A1 * | 1/2010 | Scheuermann et al. ... 424/423 |
| 2010/0152410 A1 * | 6/2010 | East et al. ............... 528/299 |
| 2010/0256748 A1 * | 10/2010 | Taylor et al. ........... 623/1.46 |

FOREIGN PATENT DOCUMENTS

| | | |
|---|---|---|
| EP | 0 341 049 A2 | 11/1989 |
| EP | 0 472 413 A2 | 2/1992 |
| WO | WO 96/11721 | 4/1996 |

OTHER PUBLICATIONS

International Search Report—PCT/US2008/074721 (Oct. 31, 2008).

* cited by examiner

*Primary Examiner* — Suzette J Gherbi
(74) *Attorney, Agent, or Firm* — Brinks Hofer Gilson & Lione

(57) ABSTRACT

An implantable drainage device for treatment of a stricture of a body vessel is disclosed. The device comprises a drainage tube including an inlet and extending to an outlet to define a drainage lumen formed through the inlet and the outlet. The drainage tube includes a swell layer and a cast layer formed about the swell layer. The swell layer has a first agent dispersed thereabout for regulated drug elution through the cast layer. The cast layer has a second agent disposed thereabout for drug elution therefrom.

16 Claims, 11 Drawing Sheets

US 7,993,411 B2

MEDICAL IMPLANT HAVING IMPROVED DRUG ELUTING FEATURES

CROSS-REFERENCE TO RELATED APPLICATIONS

This application claims the benefit of U.S. Provisional Application Ser. No. 60/969,358, filed on Aug. 31, 2007, entitled "MEDICAL IMPLANT HAVING IMPROVED DRUG ELUTING FEATURES," the entire contents of which are incorporated herein by reference.

TECHNICAL FIELD

The present invention relates to implantable medical devices. More particularly, the invention relates to stents, including stents adapted for use in the biliary tract.

BACKGROUND OF THE INVENTION

Implantation of biliary stent structures provides treatment for various conditions, such as obstructive jaundice. Biliary stenting treatment approaches can be used to provide short-term treatment of conditions such as biliary fistulae or giant common duct stones. Biliary stents may be implanted to treat chronic conditions such as postoperative biliary stricture, primary sclerosing cholangitis and chronic pancreatitis.

Although adequate, a biliary stent can become occluded once implanted within a bile duct, as an encrustation of amorphous biological material and bacteria ("sludge") accumulates on the surface of the stent, gradually obstructing the lumen of the stent. Biliary sludge is an amorphous substance often containing crystals of calcium bilirubinate and calcium palimitate, along with significant quantities of various proteins and bacteria. Sludge can deposit rapidly upon implantation in the presence of bacteria. For example, bacteria can adhere to plastic stent surfaces through pili or through production of a mucopolysaccharide coating. Bacterial adhesion to the surface of a stent lumen surface can lead to occlusion of the stent lumen as the bacteria multiply within a glycocalyx matrix of the sludge to form a biofilm over the sludge within the lumen of an implanted drainage stent. The biofilm can provide a physical barrier protecting encased bacteria from antibiotics. With time, an implanted biliary stent lumen can become blocked, thereby undesirably restricting or blocking bile flow through the biliary stent.

Once implanted, a biliary stent may also allow reflux of duodenal fluid in the common biliary duct. Such reflux may cause irritation leading to stricture of the common bile duct. Such obstruction is undesirable.

There exists a need in the art for an implantable medical device that prevents or reduces the biofilm and sludge deposition process on implantable drainage stents, such as biliary stents; and prevents or reduces reflux of duodenal fluids in the common bile duct.

BRIEF SUMMARY OF THE INVENTION

The present invention provides an implantable drainage device for treatment of a stricture of a body vessel. The device comprises a drainage tube including an inlet and extending to an outlet to define a drainage lumen formed through the inlet and the outlet. The drainage tube includes a swell layer and a cast layer formed about the swell layer. The swell layer has a first agent dispersed thereabout for regulated drug elution through the cast layer. The cast layer has a second agent disposed thereabout for drug elution therefrom.

In another example, the present invention provides a method of manufacturing an implantable drainage device for treatment of a stricture of a body vessel. The method comprises forming a tubular member with a thermoformable polymeric material. The tubular member has an inlet and extends to an outlet to define a drainage lumen formed through the inlet and outlet. The method further comprises swelling the tubular member in a swelling solution comprising a swelling solvent and a swelling solute. The swelling solute includes at least one of an antimicrobial agent and an antithrombogenic agent defining a swelled tube. The method further comprises coating the swelled tube in a casting solution comprising a casting solvent and a casting solute to define a drainage tube. The casting solute includes at least one of the antimicrobial agent, the antithrombogenic agent, and preferably a polymer.

Further objects, features, and advantages of the present invention will become apparent from consideration of the following description and the appended claims when taken in connection with the accompanying drawings.

DETAILED DESCRIPTION OF THE INVENTION

Embodiments of the present invention provide medical devices for implantation in a body vessel. Such medical devices, e.g., stents, each have a solvent swell layer and a solvent cast layer for enhanced drug eluting capabilities. Other examples of the present invention include methods of making the medical devices and methods of treatment that utilize the medical devices. Each of the solvent swell layer and the solvent cast layer contains at least one of an antimicrobial agent and an antithrombogenic agent for reduced stent clogging, lessened reflux, reduced bacteria attachment, and lessened bile film accumulation.

It is to be noted that the medical devices discussed herein are described with respect to an exemplary biliary stent embodiment comprising a solvent cast layer over a solvent swell layer. However, other medical devices, such as ureteral stents, esophageal stents or catheters can also be used as implantable medical devices according to other embodiments of the present invention.

Figure 1:
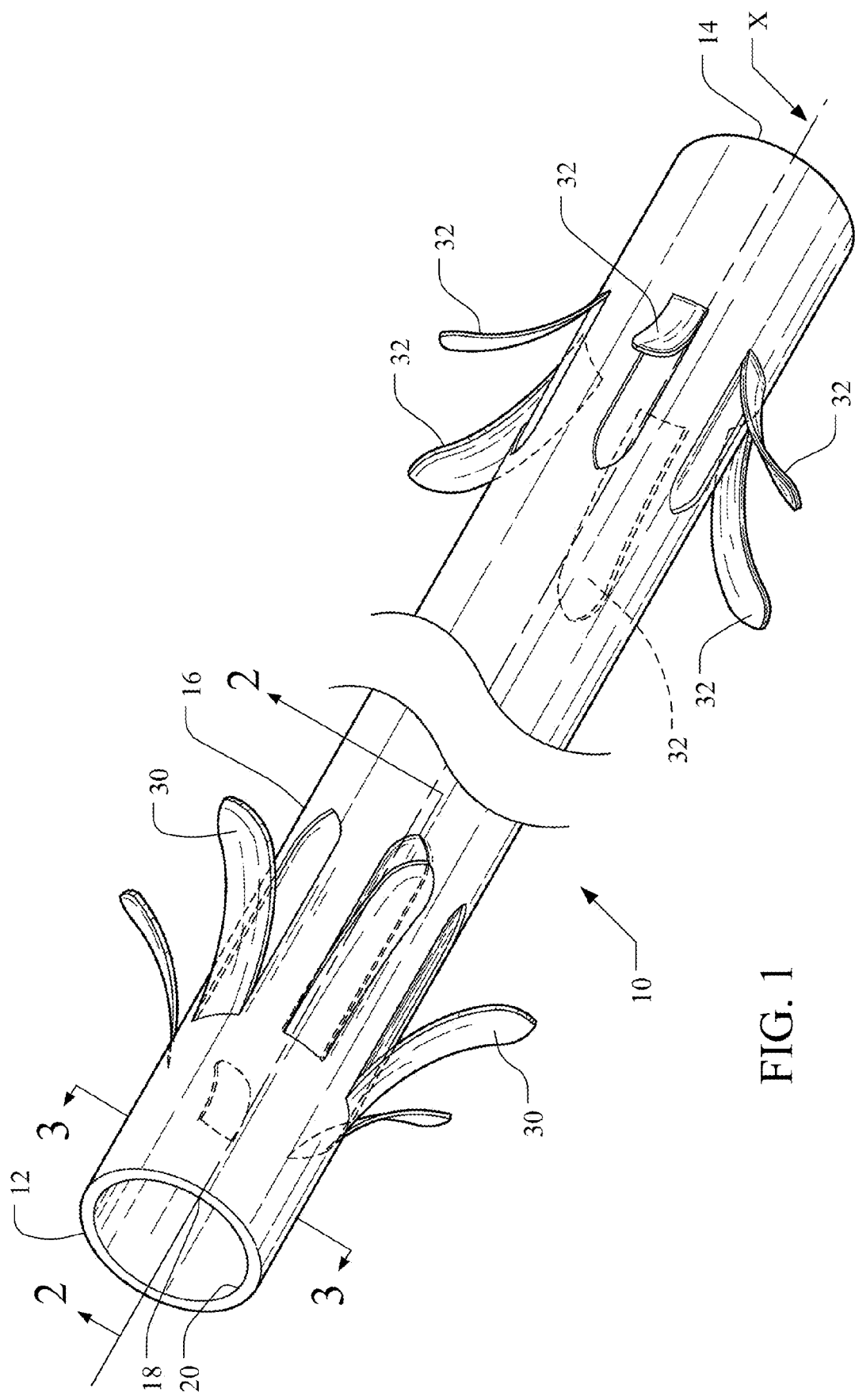
FIG. 1 is a side view of a biliary stent having improved drug eluting features in accordance with one embodiment of the present invention.

FIG. 1 illustrates an endolumenal medical device configured as a biliary stent 10 having a solvent cast layer disposed about a solvent swell layer in accordance with one embodiment of the present invention. In this embodiment, the dual-layer stent 10 provides an efficient mechanism for eluting anti-microbial and anti-thrombogenic agents therefrom within a desired body vessel. As shown, the stent 10 is a biliary drainage stent having a drainage tube 16 including a drainage lumen 18 formed therethrough from an inlet 14 to an outlet 12. Preferably, inlet 14 allows fluid to enter the drainage lumen 18 within the drainage tube 16, and outlet 12 allows fluid to exit the drainage tube 16 from the drainage lumen 18. The stent 10 is preferably configured for placement within a biliary or pancreatic duct and extends the length of the duct into the duodenum. For example, the inlet 14 of the stent 10 may be placed within a biliary or pancreatic duct. The stent 10 extends the length of the duct into the duodenum in which the outlet 12 may be placed. While the preferred embodiment describes a stent 10 intended for use in the common bile duct or pancreatic duct of a patient having a ductal occlusion or obstruction, the stent 10 may also be configured for use in other areas within the body. For example, the stent could be configured for use within a urethral, ureteral, esophageal or blood vessel.

The drainage tube 16 can be substantially straight and symmetrically disposed about a longitudinal axis X, as shown in FIG. 1. For example, diameters of about 7-12 French (2.3 mm-4.0 mm, or 0.091-0.156 inch) may be suitable external diameters for the drainage tube 16, and lengths of between about 25-180 mm (0.98-7.1 inches) may be suitable for the distance between the inlet 14 and the outlet 12.

Preferably, the medical device comprises an anchoring component to anchor the device within a body passage. The anchoring component of the biliary stent may include flaps extending from the outer surface of the drainage tube. The number, size and orientation of anchoring flaps can be modified to accommodate the migration-preventing requirements of the particular medical device to be implanted, the site of implantation and the desired function of the device. For example, the stent 10 comprises an outlet array 30 and an inlet array 32 of radially extending flaps extending from the outer surface of the drainage tube 16, proximate the outlet 12 and the inlet 14, respectively. The outlet array 30 and inlet array 32 of flaps can have any suitable number, size and configuration of flaps selected to anchor stent 10 within a biliary duct. For example, the outlet array 30 comprises one row of four flaps; the inlet array 32 comprises two rows of four flaps. The arrays of anchoring flaps 30, 32 can be formed by any suitable means such as by slicing small longitudinal sections in the distal or proximate ends of the drainage tube 16 and orienting the sliced sections radially. Preferably, the slice incisions are made on the outer surface of the tube 16 in a shallow manner so as to not create holes therethrough. Of course, in other embodiments, the slice incisions may create holes therethrough without falling beyond the scope or spirit of the present invention.

Figure 2A:
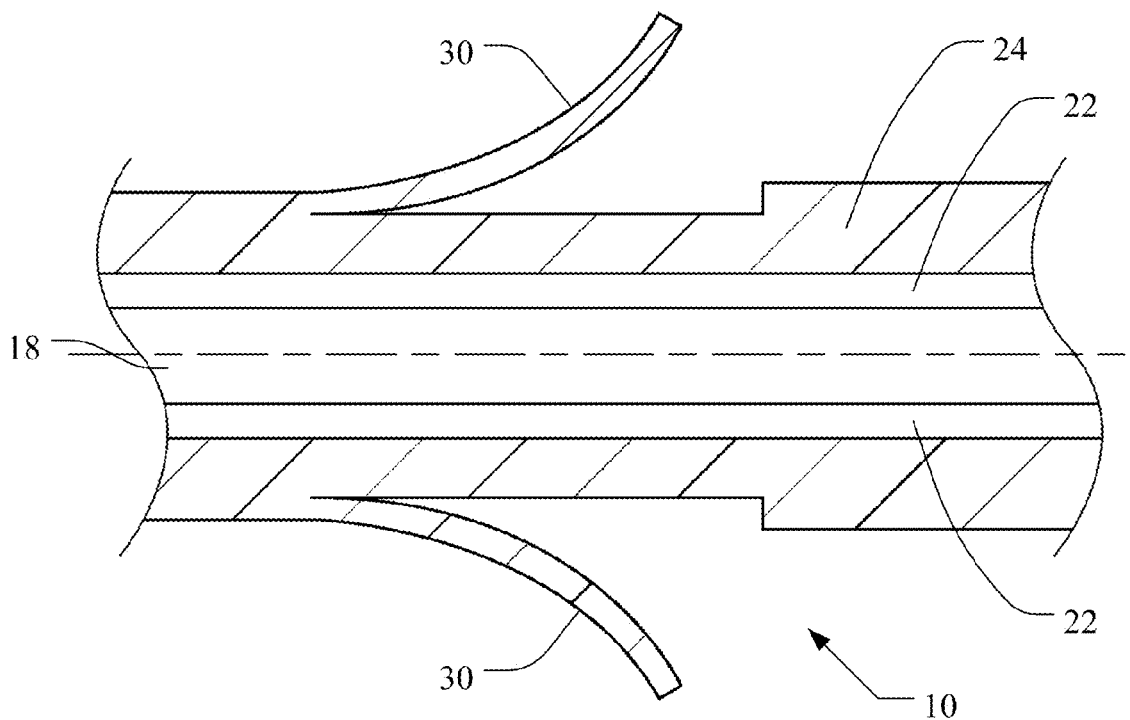
FIG. 2a is a side cross sectional view of a portion of the biliary stent in FIG. 1 taken along lines 2-2.

As shown in FIGS. 1 and 2a, the drainage tube 16 comprises an outer surface including a swell layer 22 and a cast layer 24 circumferentially disposed about the swell layer. The drainage tube 16 is preferably comprised of polymeric material that is capable of being "swelled" by penetration of a swelling solution containing a swelling solvent and a solute that includes at least one of an antimicrobial agent and an antithrombogenic agent. When applied on the outer surface of the tube, the swelling solution penetrates and "swells" the entire body of the tube. As a result, a substantially homogeneous dispersion of the antimicrobial or anti-thrombogenic agent(s) throughout the tube is observed at steady state. That is, the antimicrobial agent(s) and/or anti-thromobogenic agent(s) are able to disperse within enlarged intermolecular spaces of the body of the drainage tube when applied thereon, defining the swell layer for drug elution.

Figure 2B:
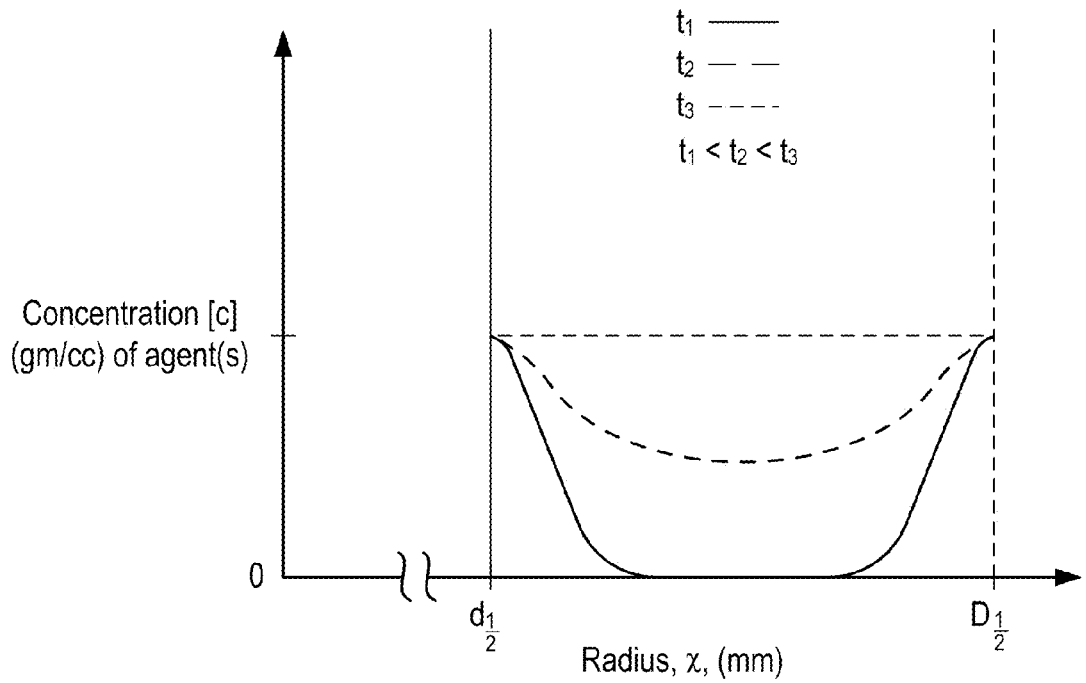
FIG. 2b is a graph depicting variable concentration of agents in swell layer as a function of swell time of a drainage tube in accordance with one example of the present invention.
Figure 2C:
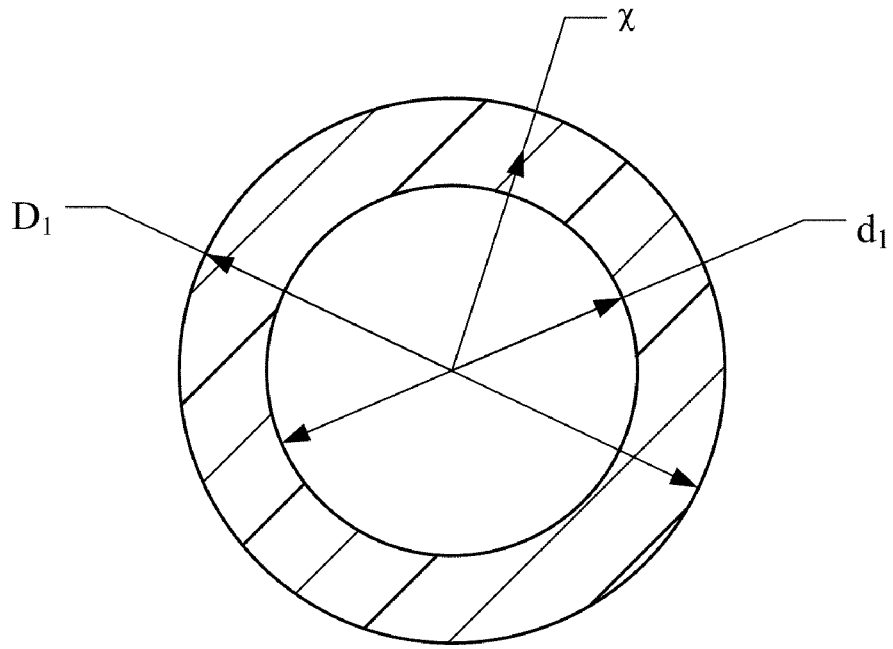
FIG. 2c is a cross-sectional view of the drainage tube corresponding to the graph of FIG. 2b.

It is to be understood that before a steady state condition is reached before the swelling/infusion process, a non-homogeneous dispersion of the antimicrobial and/or anti-thrombogenic agent(s) will be dispersed within the enlarged intermolecular spaces of the body of the drainage tube. That is, during dispersion, the concentration of solvent and agent into the polymer wall will be highest at the surface and lower in the middle until a steady state is reached. As depicted in FIGS. 2b and 2c, the inner and outer walls at $d_1$ and $D_1$, respectively, have a higher concentration of agent as the portions toward the center have a lesser concentration as a function of swelling time (t). As time increases ($t_1 < t_2 < t_3$), the concentration differences between the various portions of the wall approach zero and become negligible (steady state). As the swell process is terminated before a steady state condition is reached, a non-homogeneous condition will result.

In this embodiment, the polymeric material of the drainage tube also preferably is capable of being casted by a casting solution containing a polymer, a casting solvent and a solute that includes at least one of an antimicrobial agent and an antithrombogenic agent. When applied on the swell layer, the casting solution is able to effectively partially dissolve the polymeric material so that a cast layer may be formed circumferentially about the swell layer. Thus, the antimicrobial agent or antithrombogenic agent is incorporated onto the solidified polymeric material by solvent casting for drug elution.

The polymer of the casting solution is a polymer that is dissolved by the solvent and preferably a polymer that is known to be relatively easily dissolved by the solvent. The polymer may be the same polymer as the polymeric material discussed herein.

In one embodiment, the casting solvent comprises at least one of the following: acetone, tetrahydrofuran (THF), methyl ethyl ketone, N,N-dimethylformamide (DMF), and diemthyl sulfoxide (DMSO). Moreover, in this embodiment, the casting solute comprises at least one of the following: cephaloporins, clindamycin, chlorampheanicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin, nikko Z, phosphorylcholine, a polymer, and heparin.

Alternatively, the casting solution may contain the casting solvent, the solute, and a known monomer or a known oligomer. In this example, the monomer or oligomer will react during casting to form a polymer.

Each of the polymeric material of the drainage tube and the polymer of the casting solution (discussed herein) may be formed from elastomers such as elastomeric polyurethanes and polyurethane copolymers; silicones; polycarbonates. Mixtures or random copolymers of any of the foregoing are non-limiting examples of non-biodegradable biocompatible matrix polymers useful for manufacturing the medical devices of the present invention. Other suitable polymers are a polyolefin such as polyethylene, polypropylene, polybutylene or copolymers thereof; vinyl aromatic polymers such as polystyrene; vinyl aromatic copolymers such as styrene-isobutylene copolymers and butadiene-styrene copolymers; ethylenic copolymers such as ethylene vinyl acetate (EVA), ethylene-methacrylic acid and ethylene-acrylic acid copolymers where some of the acid groups have been neutralized with either zinc or sodium ions (commonly known as ionomers); polyacetals; chloropolymers such as polyvinylchloride (PVC); polyesters such as polyethyleneterephthalate (PET); polyester-ethers; polyamides such as nylon 6 and nylon 6,6; polyamide ethers; polyethers.

It is to be understood that there are a number of substances that may be used as the casting solvent to form the casting layer about the swell layer. Table A shows an example list of casting solvents for the casting layer.

TABLE A

Common Solvents for Casting

| Name | Structure | bp, °C. |
|---|---|---|
| acetone | 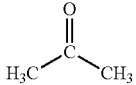 | 56 |
| tetrahydrofuran (THF) | 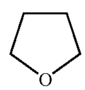 | 66 |
| methyl ethyl ketone | 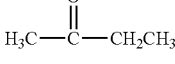 | 80 |
| N,N-dimethylformamide (DMF) | 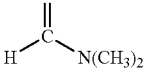 | 153 |
| diemthyl sulfoxide (DMSO) | 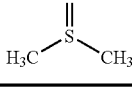 | 189 |

It is to be understood that there are a number of substances that may be used as the swell solvent to form the swelling layer. Table B shows an example list of swell solvents for the swelling layer.

TABLE B

Common Solvents for Swelling

| Name | Structure | bp, °C. |
|---|---|---|
| methanol | CH$_3$—OH | 68 |
| ethanol | CH$_3$CH$_2$—OH | 78 |
| 1-propanol | CH$_3$CH$_2$CH$_2$—OH | 97 |
| 1-butanol | CH$_3$CH$_2$CH$_2$CH$_2$—OH | 118 |
| formic acid | 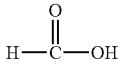 | 100 |
| acetic acid | 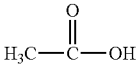 | 118 |

TABLE B-continued

Common Solvents for Swelling

| Name | Structure | bp, °C. |
|---|---|---|
| formamide | 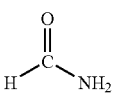 | 210 |
| acetone | 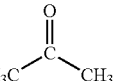 | 56 |
| tetrahydrofuran (THF) | 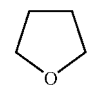 | 66 |
| methyl ethyl ketone | 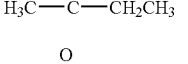 | 80 |
| ethyl acetate | 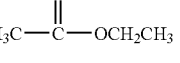 | 78 |
| acetonitrile | H$_3$C—C≡N | 81 |
| hexane | CH$_3$(CH$_2$)$_4$CH$_3$ | 69 |
| benzene | 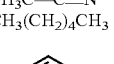 | 80 |
| diethyl ether | CH$_3$CH$_2$OCH$_2$CH$_3$ | 35 |
| methylene chloride | CH$_2$Cl$_2$ | 40 |
| Carbon tetrachloride | CCl$_4$ | 76 |
| Toluene | 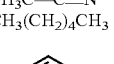 | 110 |
| Xylene | 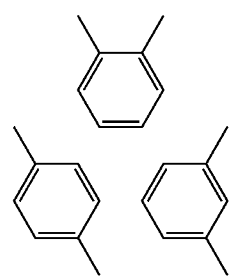 | 138 |

As shown in FIG. 2a, the drainage tube 16 forms a drainage lumen 18 centered along the longitudinal axis X of the stent 10. The drainage tube 16 is configured as a continuous uninterrupted tube adapted to provide drainage through an obstructed portion of a body vessel, such as a biliary duct.

Figure 3A:
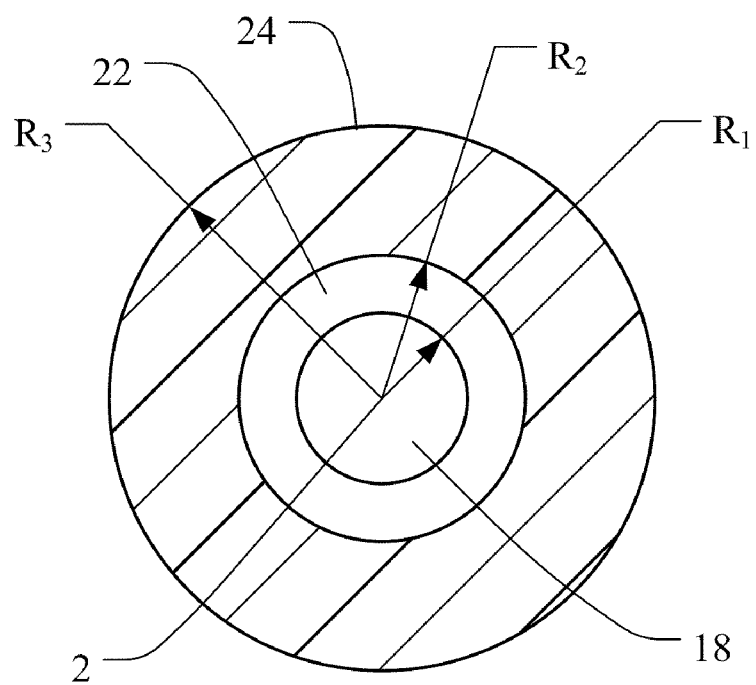
FIG. 3a is a cross sectional view of the biliary stent in FIG. 1 taken along lines 3-3.
Figure 3B:
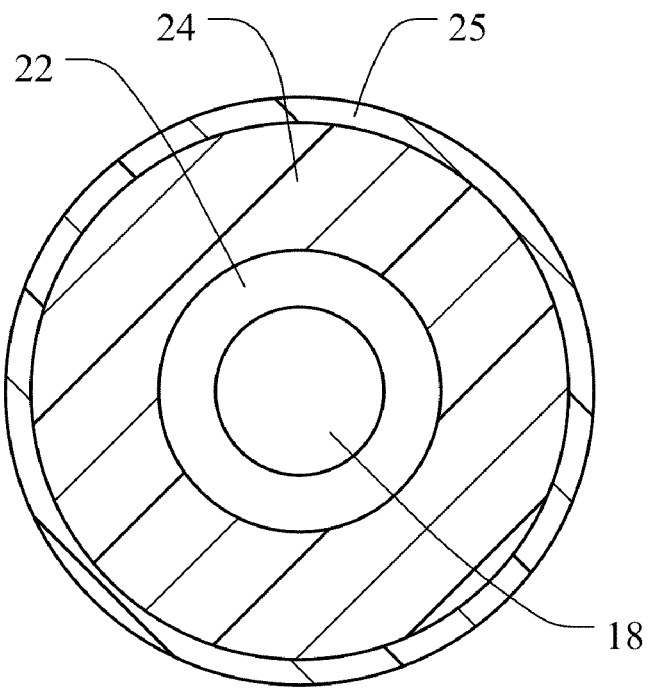
FIG. 3b is a cross-sectional view of a biliary stent having a biodegradable outer coating.

In another embodiment shown in FIG. 3b, the stent 10 may further include an outer coating 25 comprising a lubricious biodegradable coating material applied to the cast layer 24 of the drainage tube 16.

The term "antimicrobial agent" refers to a bioactive agent effective in the inhibition of, prevention of or protection against microorganisms such as bacteria, microbes, fungi, viruses, spores, yeasts, molds and others generally associated with infections such as those contracted from the use of the medical articles described herein. The antimicrobial agents include antibiotic agents and antifungal agents. The antimicrobial agent may include one of the following: cephalosporins, clindamycin, chlorampheanicol, carbapenems, minocyclines, rifampin, penicillins, monobactams, quinolones, tetracycline, macrolides, sulfa antibiotics, trimethoprim, fusidic acid and aminoglycosides. Antifungal agents include amphotericin B, azoles, flucytosine, cilofungin and nikko Z. Moreover, bactericidal nitrofuran compounds, such as those described by U.S. Pat. No. 5,599,321 (Conway et al.), incorporated herein by reference, can also be used as antimicrobials.

Examples of suitable antimicrobial materials include nanosize particles of metallic silver or an alloy of silver containing about 2.5 wt % copper (hereinafter referred to as "silver-copper"), salts such as silver citrate, silver acetate, silver benzoate, bismuth pyrithione, zinc pyrithione, zinc percarbonates, zinc perborates, bismuth salts, various food preservatives such as methyl, ethyl, propyl, butyl, and octyl benzoic acid esters (generally referred to as parabens), citric acid, benzalkonium chloride (BZC), rifamycin and sodium percarbonate. It should be noted that the agent used in the solvent swelling and solvent casting process may be the same or different drug. In each process, single or multiple kinds of antimicrobial agents may be used.

Specific non-limiting examples of suitable antibiotic agents include: ciprofloxacin, doxycycline, amoxicillin, metronidazole, norfloxacin (optionally in combination with ursodeoxycholic acid), ciftazidime, and cefoxitin. Other suitable antibiotic agents include rifampin, minocycline, novobiocin and combinations thereof discussed in U.S. Pat. No. 5,217,493 (Raad et al.). Rifampin is a semisynthetic derivative of rifamycin B, a macrocyclic antibiotic compound produced by the mold *Streptomyces mediterranic*. Rifampin is believed to inhibit bacterial DNA-dependent RNA polymerase activity and is bactericidal in nature. Rifampin is available in the United States from Merrill Dow Pharmaceuticals, Cincinnati, Ohio. Minocycline is a semisynthetic antibiotic derived from tetracycline. It is primarily bacteriostatic and is believed to exert an antimicrobial effect by inhibiting protein synthesis. Minocycline is commercially available as the hydrochloride salt which occurs as a yellow, crystalline powder and is soluble in water and slightly soluble in alcohol. Minocycline is available from Lederle Laboratories Division, American Cyanamid Company, Pearl River, N.Y. Novobiocin is an antibiotic obtained from cultures of *Streptomyces niveus* or *S. spheroides*. Novobiocin is usually bacteriostatic in action and is believed to interfere with bacterial cell wall synthesis and inhibit bacterial protein and nucleic acid synthesis. Novobiocin also appears to affect stability of the cell membrane by complexing with magnesium. Novobiocin is available from The Upjohn Company, Kalamazoo, Mich.

Bactericidal nitrofuran compounds, such as those described by U.S. Pat. No. 5,599,321 (Conway et al.), incorporated herein by reference, can also be used as an antimicrobial bioactive agent. Preferred nitrofuran bioactive agents include nitrofurantoin, nitrofurazone, nidroxyzone, nifuradene, furazolidone, furaltidone, nifuroxime, nihydrazone, nitrovin, nifurpirinol, nifurprazine, nifuraldezone, nifuratel, nifuroxazide, urfadyn, nifurtimox, triafur, nifurtoinol, nifurzide, nifurfoline, nifuroquine, and derivatives of the same, and other like nitrofurans which are both soluble in water and possess antibacterial activity. References to each of the above cited nitrofuran compounds may be found in the Merck Index, specifically the ninth edition (1976) and the eleventh edition (1989) thereof, published by Merck & Co., Inc., Rahway, N.J., the disclosures of which are each incorporated herein by reference.

The antimicrobial agent can also comprise nanosize particles of metallic silver or an alloy of silver containing about 2.5 wt % copper (hereinafter referred to as "silver-copper"), salts such as silver citrate, silver acetate, silver benzoate, bismuth pyrithione, zinc pyrithione, zinc percarbonates, zinc perborates, bismuth salts, various food preservatives such as methyl, ethyl, propyl, butyl, and octyl benzoic acid esters (generally referred to as parabens), citric acid, benzalkonium chloride (BZC), rifamycin and sodium percarbonate.

Another example of a suitable antimicrobial agent is described in published U.S. patent application US2005/0008763A1 (filed Sep. 23, 2003 by Schachter), incorporated herein by reference.

It is also to be understood that the antithrombogenic agent mentioned above may include any suitable antithrombogenic agent known in the art such as phosphorylcholine and heparin, to reduce thrombus formation about the device while in a body vessel of a patient.

In one embodiment (FIG. 3a), the radial thicknesses of the swell layer ($R_2-R_1$) and cast layer ($R_3-R_2$) of the drainage tube 16 may be varied. In one aspect, the combined radial thickness of swell layer and the cast layer together ($R_3-R_1$) can be kept constant, while varying the radial thicknesses of the swell layer and the cast layer. The radial thickness of the swell layer can be selected to provide the stent with a desired amount of flexibility or rigidity for an intended application. The radial thickness and composition of the cast layer can be selected to provide a desired rate of drug elution therethrough.

Referring to FIG. 3a, the outer radius $R_3$ may be measured as the radial distance from the longitudinal axis X to the outer surface of the tube. $R_1$ is the radius of the drainage lumen 18. The thickness of the swell layer depends on the material selected, and can be any thickness providing a desired amount of radial support, while retaining a desired level of flexibility. For example, a polyurethane biliary stent swell layer may have a thickness of about 0.2 mm (0.01-inch) to about 1.0 mm (0.04-inch), preferably about 0.4 mm (0.02-inch) for a 10 F stent. Values for the radius $R_1$ for a biliary stent can vary from about 0.5 mm (0.02-inch) to about 1.5 mm (0.06-inch) for a 10 F stent, and from about 0.25 mm (0.01-inch) to about 0.75 mm (0.03-inch) for a 5 F stent. The drainage lumen 18 is preferably configured to maximize the surface area of the swell layer defining the drainage lumen 18. Generally, the total radial thickness of the swell layer and the cast layer will be about 0.4 mm (0.02-inch) to about 1.5 mm (0.06-inch), preferably between about 0.6 mm (0.06-inch) and about 1.0 mm (0.04-inch). The radial thicknesses of the swell layer and the cast layer can be selected to provide at least a minimal desired amount of radial strength to maintain patency of the drainage lumen 18 upon implantation.

The ratio of the radial thickness of the swell layer to the radial thickness of the cast layer is preferably less than about 20:1—more preferably less than about 10:1, 5:1, 3:1 or 2:1 and most preferably about 1:1—prior to implantation of the drainage stent within a biliary or pancreatic duct. One preferred biliary stent provides a polyurethane swell layer having a radial thickness of about 1.75 mm (0.07-inch). As the inner surfaces and outer surfaces of the device may be masked by known means, it is understood that one of the surfaces may be selectively masked to treat the other surface without falling beyond the scope or spirit of the present invention.

Figure 3C:
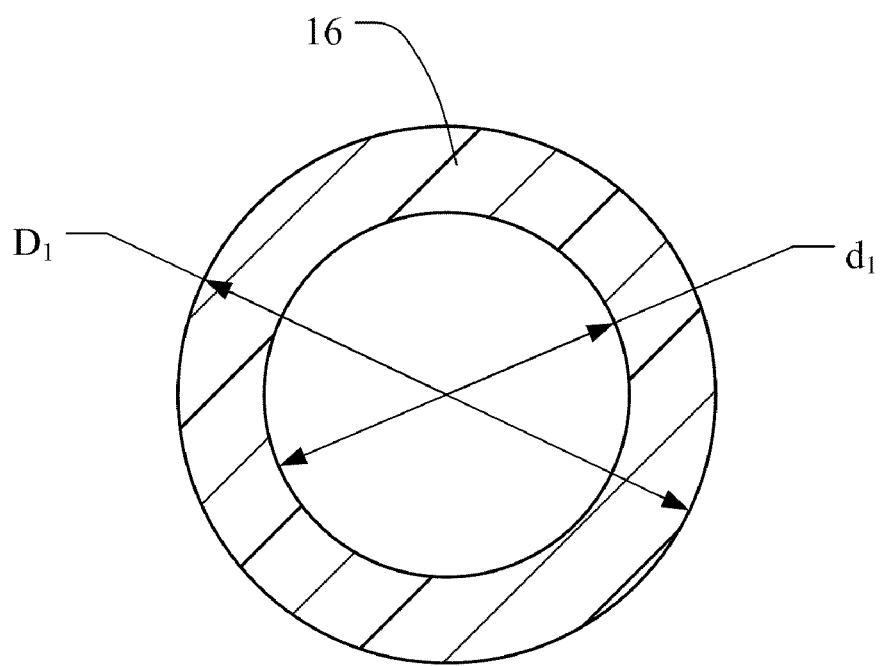
FIG. 3c is a cross-sectional view of a biliary stent before swell treatment in accordance with one embodiment of the present invention.
Figure 3D:
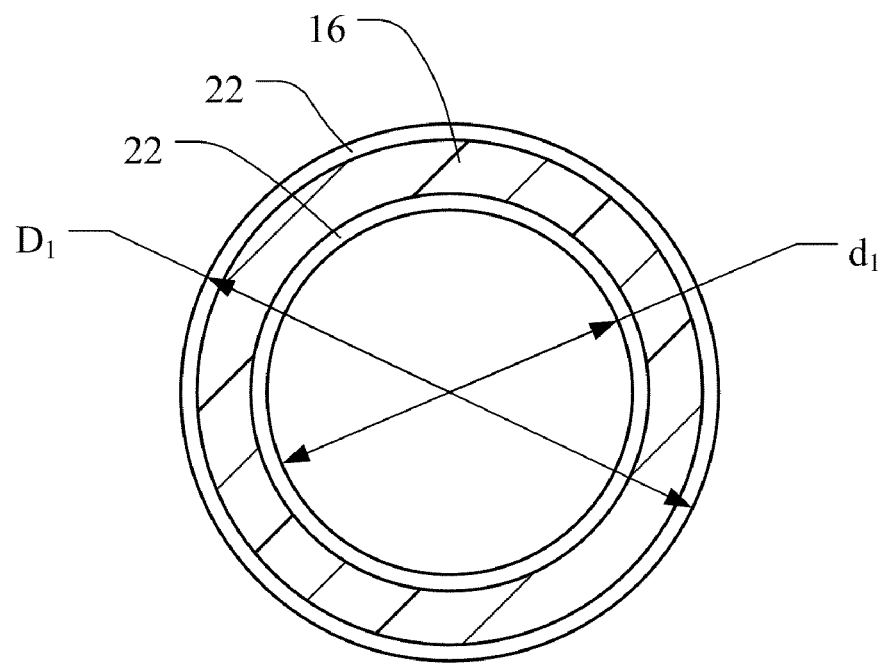
FIG. 3d is a cross-sectional view of the biliary stent after swell treatment.
Figure 3E:
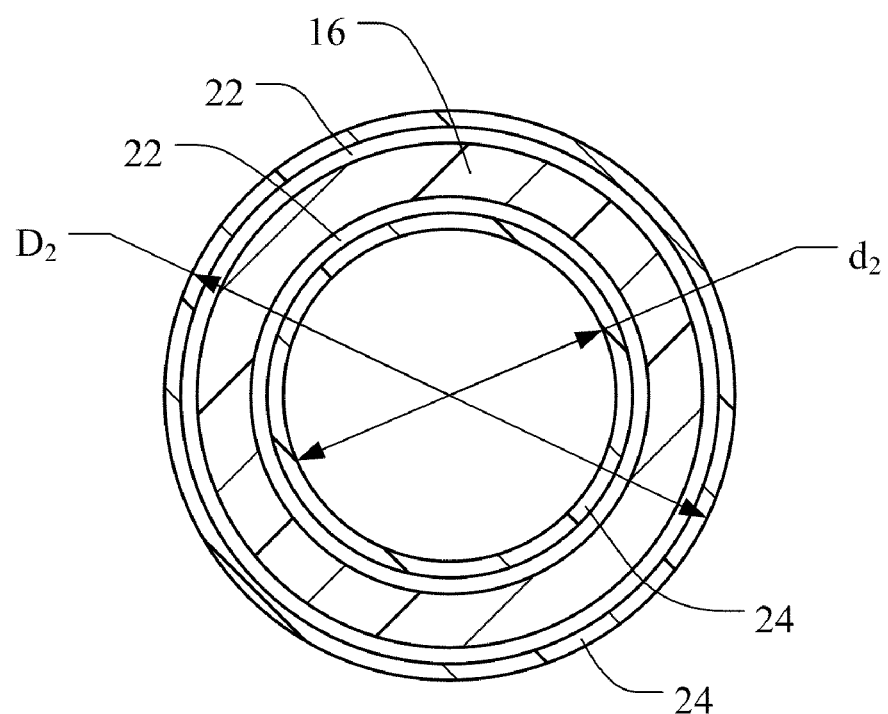
FIG. 3e is a cross-sectional view of the biliary stent after casting.

It is understood that the swelling treatment may not affect dimensions whereas coating with casting solution may affect dimensions. For example, in FIGS. 3c and 3d, diameters $d_1$ and $D_1$ were not affected when the swell layer 22 was applied to the tube or base polymer 16. In this example, the solvent swells the polymer and loosens the polymeric chains and the agent dissolves in the solvent. In FIGS. 3c-3e, diameters $d_1$ and $D_1$ were affected and now are represented by diameters $d_2$ and $D_2$, respectively, where diameters $d_1 > d_2$ and $D_1 > D_2$. This is due to the application of the casting layer to the device.

In use, the cast layer is preferably configured to a relatively slow release of anti-microbial and/or anti-thrombogenic agent(s) therefrom. The swell layer, on the other hand, is configured to relatively quickly release antimicrobial and/or anti-thrombogenic agents therefrom. The disposition of the cast layer causes the cast layer to act as a decelerator to the drug release from the swell layer to slow the rate of drug elution therefrom. This provides an enhanced device for drug elution into a body vessel.

Figure 4:
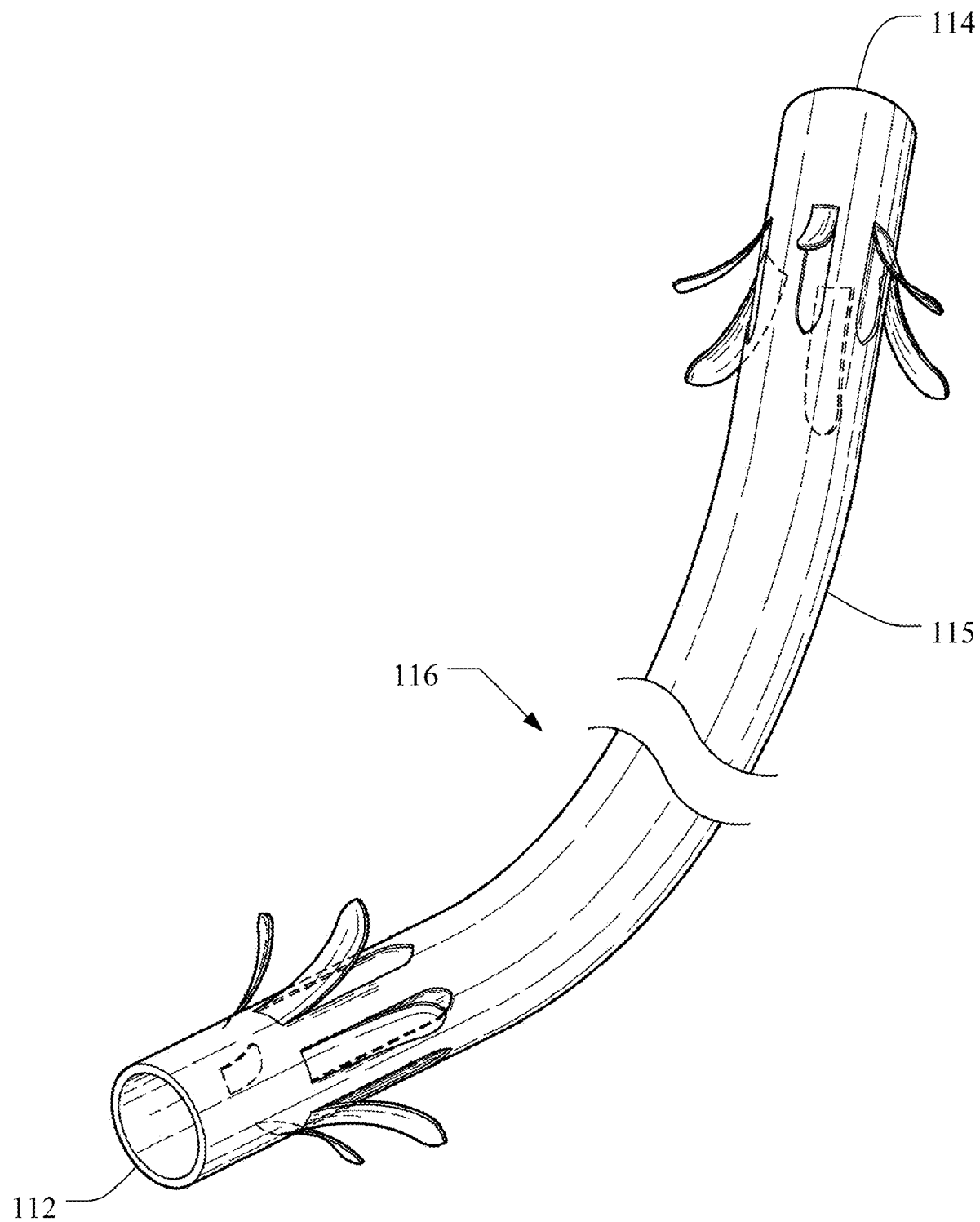
FIG. 4 is a side view of a biliary stent having improved anti-reflux features in accordance with another embodiment of the present invention.

FIG. 4 illustrates a device 110 comprising a drainage tube 116 having one or more bends. In this embodiment, the drainage tube 116 includes a bend 115 positioned about mid way between the outlet 112 and the inlet 114, so as to accommodate the anatomical structure of a biliary duct. The bend preferably conforms to the duodenal anatomy, and can be about 120 degrees. Alternatively, the bend can be positioned about ⅓ of the distance from the inlet 114 and the outlet 112.

Figure 5:
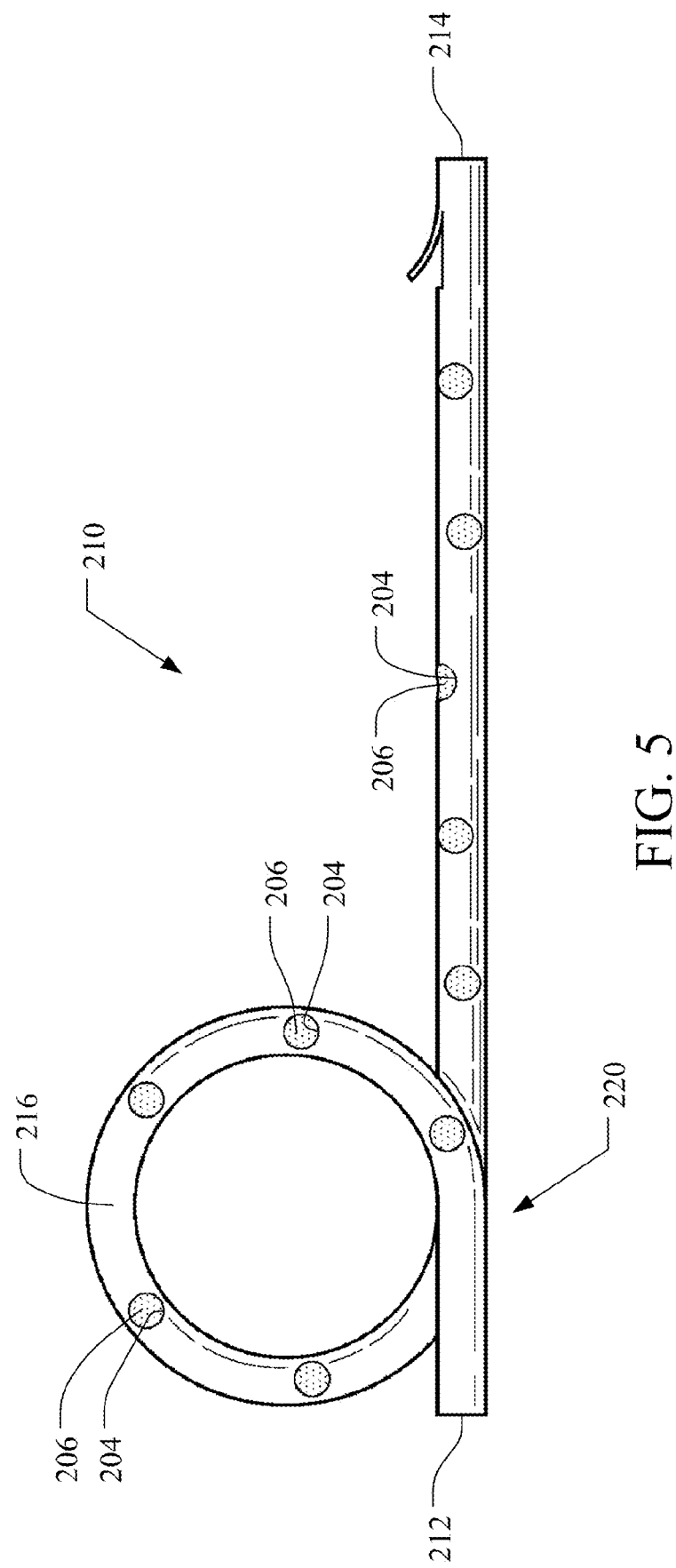
FIG. 5 is a side view of a biliary stent having improved drug eluting features in accordance with yet another embodiment of the present invention.

FIG. 5 illustrates a medical device 210 comprising a drainage tube 216 having any particular shape, e.g., a "pigtail" configuration 220, in accordance with another embodiment of the present invention. In this example, the device 210 comprises a swell layer (as mentioned above) and a polymeric layer disposed about the swell layer. Preferably, the swell layer is a layer that is swelled with a swelling solution (as discussed above). In this embodiment, the polymeric layer is not solvent casted. As shown, the polymeric layer comprises a plurality of pores formed radially through the polymeric layer to expose the swell layer of the drainage tube 216. As shown, the pores 204 are filled or "plugged" with biodegradable material 206 that degrades when implanted in a body vessel of a patient. In use, as the biodegradable plugs dissolve or degrade within a body vessel, the swell layer is exposed thereby activating drug elution from the swell layer into the body vessel. Thus, degradation of the plugs "turns-on" exposure of the underlayer or swelled layer as the over-layer or outer polymeric layer becomes depleted.

Figure 6:
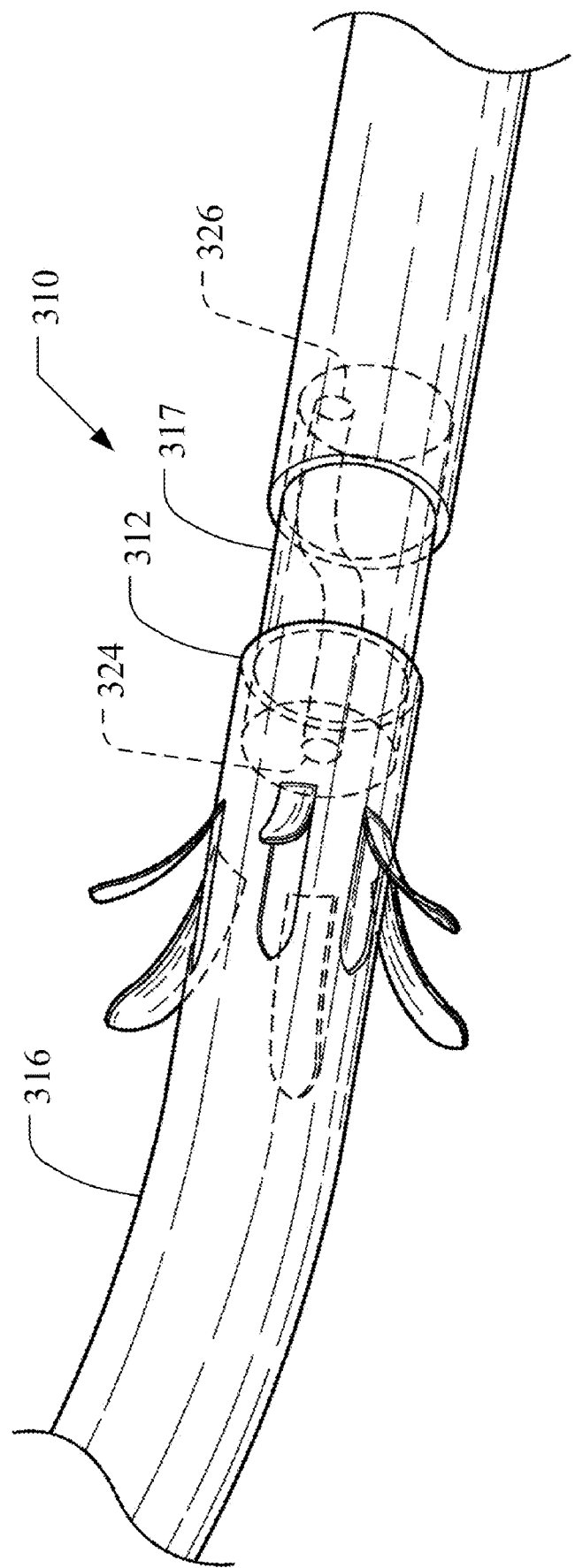
FIG. 6 is a perspective view of a medical device having improved drug eluting and reduced backflow features in accordance with another embodiment of the present invention.

FIG. 6 illustrates a device 310 comprising a drainage tube 316 having an anti-reflux member 317 cooperable and attached to an outlet 312 of the drainage tube 316. The drainage tube 316 comprises components similar to the drainage tube 16 mentioned above. In this embodiment, the anti-reflux member 317 comprises an inlet bore 324 and an outlet bore 326 in fluid communication with the inlet bore 324. As shown, the inlet and outlet bores 324, 326 are in non-alignment relationship to prevent backflow from the outlet bore 326 through the inlet bore 324 during use of the device.

The drainage tube can be formed from any suitable biocompatible and biostable material. The tube is preferably resiliently compliant enough to readily conform to the curvature of the duct in which it is to be placed, while having sufficient "hoop" strength to retain its form within the duct. Preferably, the tube is formed from a thermoformable material that can be coextruded in a separate layer with a biodegradable material (discussed below).

One suitable drainage tube is the COTTON-LEUNG® (Amsterdam) Biliary Stent (Cook Endoscopy Inc., Winston-Salem, N.C., USA). Examples of suitable drainage tubes having a bent configuration include: COTTON-HUIBREGTSE® Biliary Stents, COTTON-LEUNG® (Amsterdam) Stents, GEENEN® Pancreatic Stents, ST-2 SOE-HENDRA TANNENBAUM Biliary Stents and JOHLIN® Pancreatic Wedge Stents, all commercially available from Wilson-Cook Medical Inc. (Winston-Salem, N.C., USA). Examples of suitable stents 10 having a coiled ("pigtail") inlet and outlet configuration include: Double Pigtail Stent, the ZIMMON® Biliary Stent and the ZIMMON® Pancreatic Stents, all commercially available from Wilson-Cook Medical Inc. (Winston-Salem, N.C., USA).

The endolumenal medical device may include a means for orienting or viewing the orientation or position of the medical device within a body vessel. For example, an endolumenal medical device or a medical device delivery system can comprise radiopaque indicia providing information on the position or the orientation of the medical device within a body vessel. An endolumenal medical device or delivery device may comprise one or more radiopaque materials to facilitate tracking and positioning of the medical device. The radiopaque materials may be added in any fabrication method or absorbed into or sprayed onto the surface of part or all of the medical device to form one or more marker bands. A marker band may be formed from a suitably radiopaque material. Radiopacity may be imparted to the marker band by covalently binding iodine to the polymer monomeric building blocks of the elements of the medical device. Common radiopaque materials include barium sulfate, bismuth subcarbonate, and zirconium dioxide. Other radiopaque elements include: cadmium, tungsten, gold, tantalum, bismuth, platinum, iridium, and rhodium. In one preferred embodiment, iodine may be employed for its radiopacity and antimicrobial properties. Radiopacity is typically determined by fluoroscope or x-ray film. Imagable markers, formed from radiopaque material, can be incorporated in any portion of a medical device. For example, radiopaque markers can be used to identify a long axis or a short axis of a drainage tube within a body vessel. A radiopaque material may be attached to a drainage tube of a drainage stent. The marker band can provide a means for orienting endolumenal medical device within a body lumen. The marker band can be identified by remote imaging methods including X-ray, ultrasound, Magnetic Resonance Imaging and the like, or by detecting a signal from or corresponding to the marker. For example, marker bands may be provided at one or both of the inlet and outlet of a biliary drainage stent.

As mentioned above, the device may include a biodegradable coating disposed thereon. The biodegradable coating may include one or more coating layers that dissolve over a desired time within the body in a manner that is biocompatible. Dissipation (e.g., by dissolution or degradation) of the biodegradable coating material can result in "flaking off" of sludge components such as bacteria or biofilm that may have accumulated on the surface of the layer after implantation. Therefore, the actual diameter of drainage lumen 18 can increase over time, as more of the biodegradable coating dissipates.

The biodegradable material can comprise any suitable biodegradable material that can be degraded and absorbed by the body over time to gradually remove (e.g., by "flaking off") sludge accumulation within, and enlarge, the drainage lumen 18 over time. A number of other biodegradable homopolymers, copolymers, or blends of biodegradable polymers can be included in the biodegradable coating. These include, but are not necessarily limited to, polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethylene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

The biodegradable coating may include one or more biodegradable materials, selected from the group consisting of: a hydrogel, an elastin-like peptide, a polyhydroxyalkanoates (PHA), polyhydroxybutyrate compounds, and co-polymers and mixtures thereof. The biodegradable material can be selected and varied based on various design criteria. The biodegradable material preferably comprises one or more hydrolyzable chemical bonds, such as an ester, a desired degree of crosslinking, a degradation mechanism with minimal heterogeneous degradation, and nontoxic monomers. The biodegradable material may be a polyhydroxyalkanoate compound, a hydrogel, poly(glycerol-sebacate) or an elastin-like peptide. The biodegradable material may comprise a poly-α-hydroxy acid, such as polylactic acid (PLA). PLA can be a mixture of enantiomers typically referred to as poly-D, L-lactic acid. Alternatively, the biodegradable material is poly-L(+)-lactic acid (PLLA) or poly-D(−)-lactic acid (PDLA), which differ from each other in their rate of biodegradation. PLLA is semicrystalline. In contrast, PDLA is amorphous, which can promote the homogeneous dispersion of an active species. Unless otherwise specified, recitation of "PLA" herein refers to a biodegradable polymer selected from the group consisting of: PLA, PLLA and PDLA.

In another example, the biodegradable material includes a polyhydroxyalkanoate biodegradable polymer such as polylactic acid (poly lactide), polyglycolic acid (poly glycolide), polylactic glycolic acid (poly lactide-co-glycolide), poly-4-hydroxybutyrate, or a combination of any of these. Suitable biodegradable polymers include poly-L-lactide (PLLA), poly-D-lactide (PDLA), polyglycolide (PGA), copolymers of lactide and glycolide (PLGA), polydioxanone, polygluconate, polylactic acid-polyethylene oxide copolymers, modified cellulose, collagen, poly(hydroxybutyrate), polyanhydride, polyphosphoester, poly(amino acids) or related copolymers, each of which have a characteristic degradation rate in the body. For example, PGA and polydioxanone are relatively fast-bioabsorbing materials (weeks to months) and PLLA and polycaprolactone are a relatively slow-bioabsorbing material (months to years). Thus, a skilled person will be able to choose an appropriate biodegradable material, with a degradation rate that is suitable for a desired application.

The biodegradable material may also comprise polyglycolic acid (PGA). Polyglycolic acid is a simple aliphatic polyester that has a semi-crystalline structure, and substantially degrades in 3 months. Compared with PLA, PGA is a stronger acid and is more hydrophilic, and thus more susceptible to hydrolysis. PLA is generally more hydrophobic than PGA, and undergoes a complete mass loss in 1 to 2 years. A summary of the properties of some desirable biodegradable material polymers are shown below in Table C.

TABLE C

| Biodegradable Materials | | |
|---|---|---|
| Polymer | Crystallinity | Degradation Rate (depends on molecular weight of polymer) |
| PGA | High Crystallinity | 2-3 months |
| PLLA | Semi-crystalline | >2 years |

TABLE C-continued

| Biodegradable Materials | | |
|---|---|---|
| Polymer | Crystallinity | Degradation Rate (depends on molecular weight of polymer) |
| PDLA | Amorphous | 12-16 months |
| PLGA | Amorphous | 1-6 months (depends on ratio of LA to GA) |

The composition of the biodegradable coating may be selected to provide a degradation rate that is suitable for a desired application. The molecular weight of the biodegradable material can be selected to provide desired rates of bioabsorption and desired physical properties, such as radial strength, for the device. For example, PGA and polydioxanone are relatively fast-bioabsorbing materials (weeks to months) and PLLA and polycaprolactone are a relatively slow-bioabsorbing material (months to years). The biodegradable material can also be a polylactic glycolic acid (PLGA), or other copolymers of PLA and PGA. The properties of the copolymers can be controlled by varying the ratio of PLA to PGA. For example, copolymers with high PLA to PGA ratios generally degrade slower than those with high PGA to PLA ratios. PLGA degrades slightly faster than PLA. The process of lactic acid hydrolysis can be slower than for the glycolic acid units of the PLGA co-polymer. Therefore, increasing the PLA:PGA ratio in a PLGA co-polymer generally results in a slower rate of in vivo bioabsorption of a PLGA polymer.

The biodegradable material should be strong enough to withstand mechanical stress or strain anticipated during delivery and upon implantation within the body. The molecular weight of the polymer(s) should be high enough to provide sufficient durability so that the polymers will not be rubbed off during sterilization, handling, or deployment of the medical device and will not crack when the device is expanded. Exemplary polymer systems that may also be used in one or more coating layers include polymers that are biocompatible when the medical device is implanted. Preferably, the molecular weight of the biodegradable material is about 50-500 kDa, or higher. Generally, mechanical properties of polymers increase with increasing molecular weight. For instance, the strength and tensile modulus of PLLA generally increases with increasing molecular weight. PLLA, PDLA and PGA include tensile strengths of from about 40 thousands of pounds per square inch (psi) (276 MPa) to about 120 psi (827 MPa), a tensile strength of 80 psi (552 MPa) is typical and a preferred tensile strength is from about 60 psi (414 MPa) to about 120 psi (827 MPa).

The endolumenal medical devices can be formed in any suitable manner that provides the drainage tube defining at least a portion of the drainage lumen. The drainage tube is preferably a thermoformable, non-biodegradable material providing a desired level of mechanical strength to the medical device. Preferably, the drainage tube is formed by an extrusion process. The drainage tube may also be formed by other processing and shaping techniques such as laminar injection molding (LIM) technology. For example, a polymer to be extruded may be brought to an elevated temperature above its melting point. PLLA, for instance, may be heated to between 210° C. and 230° C. The polymer is then extruded at the elevated temperature into a continuous generally flat film using a suitable die, at a rate of about three to four feet per minute. The continuous film may then be cooled by passing the film through a nucleation bath of water.

The drainage tube may then undergo a solvent swell process. For example, the drainage tube may be soaked in a swelling solution mentioned above at between about 30° C. and 60° C., more preferably about 40 and 45° C., and containing a swelling solvent and a solute that includes at least one of an antimicrobial agent and an antithrombogenic agent mentioned above. The drainage tube may be soaked for between about 30 and 50 minutes. When applied on the outer surface of the tube, the swelling solution penetrates and "swells" the entire body of the tube. As a result, a substantially homogeneous dispersion of the antimicrobial or antithrombogenic agent(s) throughout the tube is observed at steady state. The drainage tube is then rinsed with purified water and air dried. Upon drying, the swelling solvent is evaporated from the tube while leaving the antimicrobial or antithrombogenic agent within the matrix of the polymeric material comprising the drainage tube. That is, the antimicrobial agent(s) and/or anti-thromobogenic agent(s) are able to disperse within enlarged intermolecular spaces of the body of the drainage tube when applied thereon, defining the swell layer for drug elution.

The drainage tube may then be casted by a casting solution at between about 30° C. and 60° C., more preferably about 40° C. and 45° C., and containing a solute that includes at least one of an antimicrobial agent and an antithrombogenic agent. The casting solution may be applied thereon by any suitable matter, e.g., dipping or spraying. When applied on the swell layer, the casting solution is able to effectively partially dissolve the polymeric material of the drainage tube so that a cast layer may be formed circumferentially about the swell layer. The drainage tube is then rinsed with purified water and air dried. Upon drying, the casting solvent is evaporated from the tube while leaving the antimicrobial or antithrombogenic agent within the matrix of the polymeric material comprising the drainage tube. Thus, the antimicrobial agent or antithrombogenic agent is incorporated or casted about the solidified polymeric material by solvent casting for drug elution.

The endolumenal medical device can be delivered to a point of treatment within a body vessel in any suitable manner. Preferably, the endolumenal medical device is delivered endoscopically. For example, a biliary stent can be inserted into a biliary lumen in one of several ways: by inserting a needle through the abdominal wall and through the liver (a percutaneous transhepatic cholangiogram or "PTC"), by cannulating the bile duct through an endoscope inserted through the mouth, stomach, and duodenum (an endoscopic retrograde cholangiogram or "ERCP"), or by direct incision during a surgical procedure. A preinsertion examination, PTC, ERCP, or direct visualization at the time of surgery may be performed to determine the appropriate position for stent insertion. A guidewire can then be advanced through the lesion; a delivery catheter is passed over the guidewire to allow the stent to be inserted. In general, plastic stents are placed using a pusher tube over a guidewire with or without a guiding catheter.

Delivery systems are now available for plastic stents that combine the guiding and pusher catheters (OASIS, Wilson-Cook Medical Inc., Winston-Salem, N.C.). The stent may be placed in the biliary duct either by the conventional pushing technique or by mounting it on a rotatable delivery catheter having a stent engaging member engageable with one end of the stent. Typically, when the diagnostic exam is a PTC, a guidewire and delivery catheter may be inserted via the abdominal wall. If the original exam was an ERCP, the stent may be placed via the mouth. The stent may then positioned under radiologic, endoscopic, or direct visual control at a point of treatment, such as across the narrowing in the bile duct. The stent may be released using the conventional pushing technique. The delivery catheter may then be removed, leaving the stent to hold the bile duct open. A further cholangiogram may be performed to confirm that the stent is appropriately positioned. Alternatively, other endolumenal medical devices can also be delivered to any suitable body vessel, such as a vein, artery, urethra, ureteral passage or portion of the alimentary canal.

As used herein, the term "body vessel" means any body passage cavity that conducts fluid, including but not limited to biliary ducts, pancreatic ducts, ureteral passages, esophagus, and blood vessels such as those of the human vasculature system.

As used herein, the term "implantable" refers to an ability of a medical device to be positioned at a location within a body, such as within a body vessel. Furthermore, the terms "implantation" and "implanted" refer to the positioning of a medical device at a location within a body, such as within a body vessel.

As used herein, "endolumenally," "intraluminal" or "transluminal" all refer synonymously to implantation placement by procedures wherein the prosthesis is advanced within and through the lumen of a body vessel from a remote location to a target site within the body vessel. Endolumenal delivery includes implantation in a biliary duct from an endoscope or catheter.

As used herein, "circumferentially enclose" or "circumferentially disposed" means to form a perimeter having any desired cross-sectional configuration. The circumferentially enclosing or disposed structure forms a perimeter around a circumferentially enclosed structure, with or without physically contacting the circumferentially enclosed structure. The material forming the circumferentially enclosing structure may have any suitable surface morphology, and may include smooth or rough surfaces. The circumferentially enclosing structure perimeter may have any cross sectional configuration, but preferably has a circular or elliptical cross sectional shape. One preferred embodiment provides a drainage stent having a support member circumferentially enclosing a biodegradable coating with one or more drainage lumen extending through the biodegradable coating.

A "biocompatible" material is a material that is compatible with living tissue or a living system by not being toxic or injurious and not causing immunological rejection.

The term "biodegradable" is used herein to refer to materials selected to dissipate upon implantation within a body, independent of which mechanisms by which dissipation can occur, such as dissolution, degradation, absorption and excretion. The actual choice of which type of materials to use may readily be made by one ordinarily skilled in the art. Such materials are often referred to by different terms in the art, including "bioresorbable," "bioabsorbable," or "biodegradable," depending upon the mechanism by which the material dissipates. For the purposes of this application, unless otherwise specified, the term "biodegradable" includes materials that are "bioresorbable," and "bioabsorbable." The prefix "bio" indicates that the erosion occurs under physiological conditions, as opposed to other erosion processes, caused by, for example, high temperature, strong acids and/or bases, UV light or weather conditions. As used herein, "biodegradable material" includes materials, such as a polymer or copolymer, that are absorbed by the body, as well as materials that degrade and dissipate without absorption into the body. As used herein, "biodegradable polymer" refers to a polymer or copolymer which dissipates upon implantation within the body. A large number of different types of materials are known in the art which may be inserted within the body and later dissipate.

Figure 7:
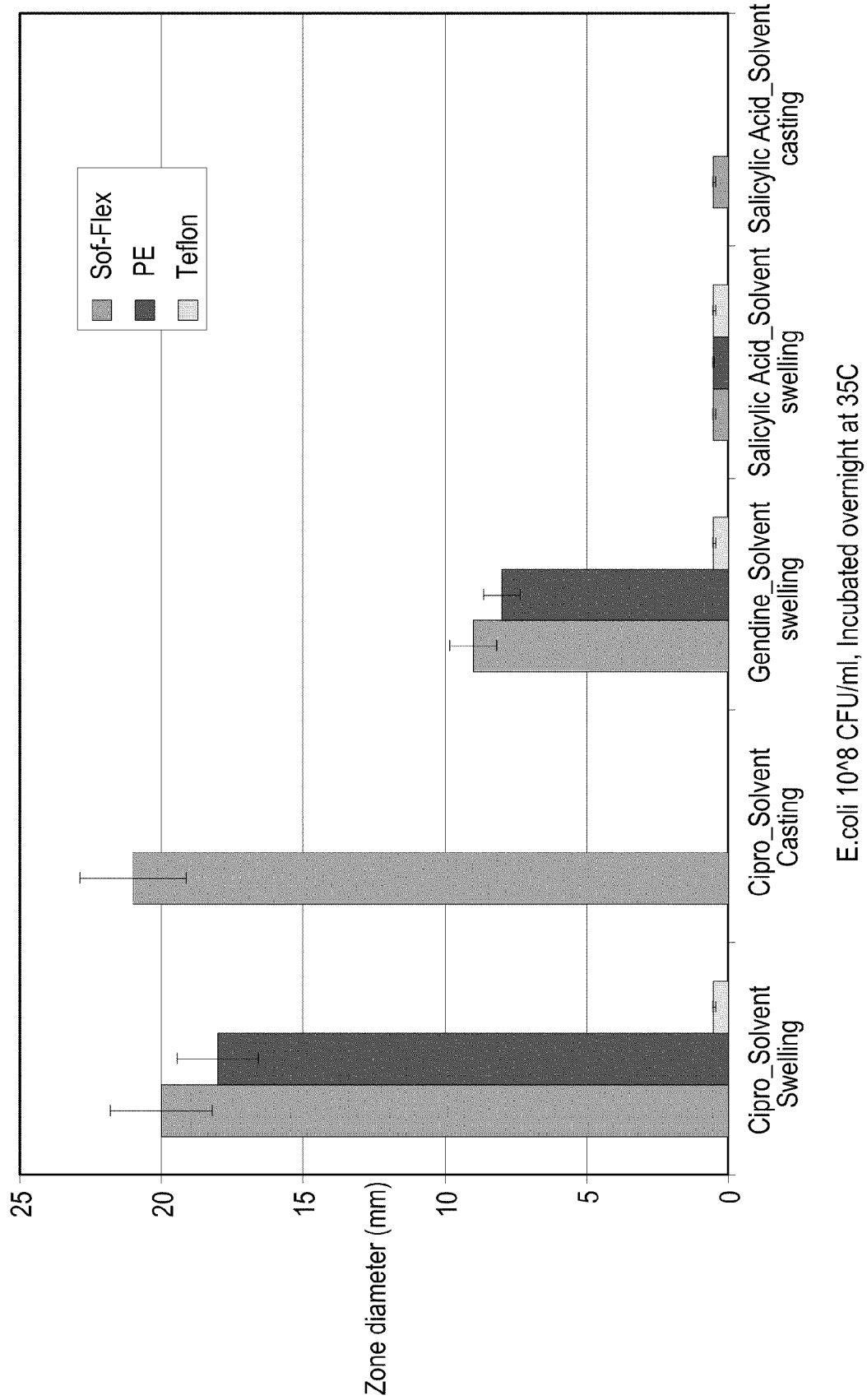
FIGS. 7-9 are graphs depicting drug elution behaviors.

Graph 1 (FIG. 7) provided below depicts the following: (1) ciprofloxacin is very effective in inhibiting *E. coli*; which is not sensitive to Salicylic Acid; and (2) coating methods (Solvent Swelling and Solvent Casting) used in this study are equally good in either polyurethane or polyethylene materials. However, those methods did not show desirability in Teflon material. Note the Zone Diameter as known in the art refers to the size of Inhibited Ring in which the tested bacteria is inhibited to grow.

Figure 8:
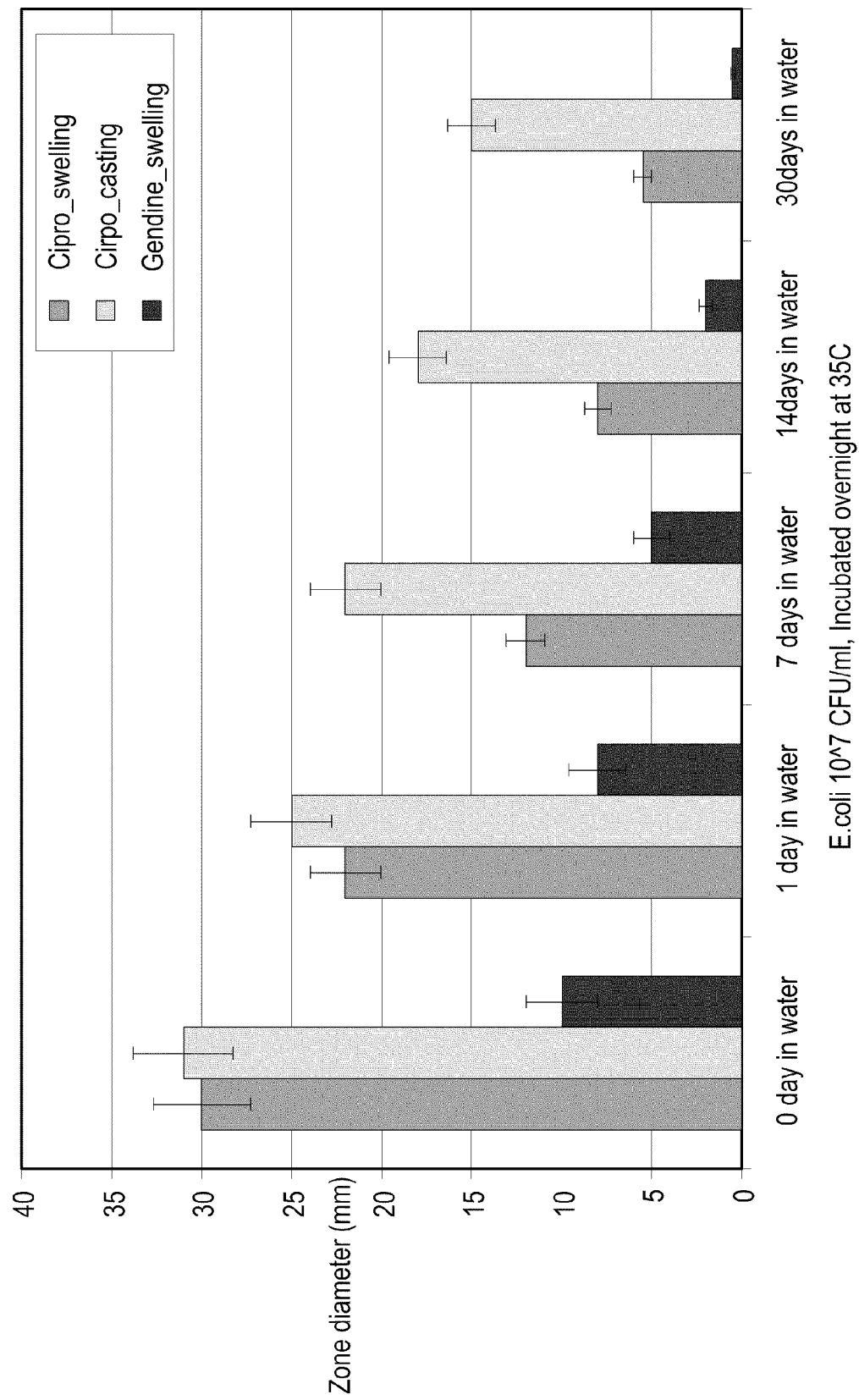

Graph 2 (FIG. 8) below depicts that drug elution behaviors of ciprofloxacin coated plastic stent. Those drug-coated plastic stents were soaked in water for a period of time before being tested in a bacteria inhibition experiment. Based on Graph 2, it has been concluded that: (1) it appears that solvent-swelling coating method is advantageous for short-term applications, since the Zone Diameter dropped to less than 10 mm after the drug-coated sample being soaked in water for 14 days; and it appears that that solvent-casting coating method may be advantageous for long-term application, since the Zone Diameter was still more than 15 mm after being soaked in water for 30 days.

Figure 9:
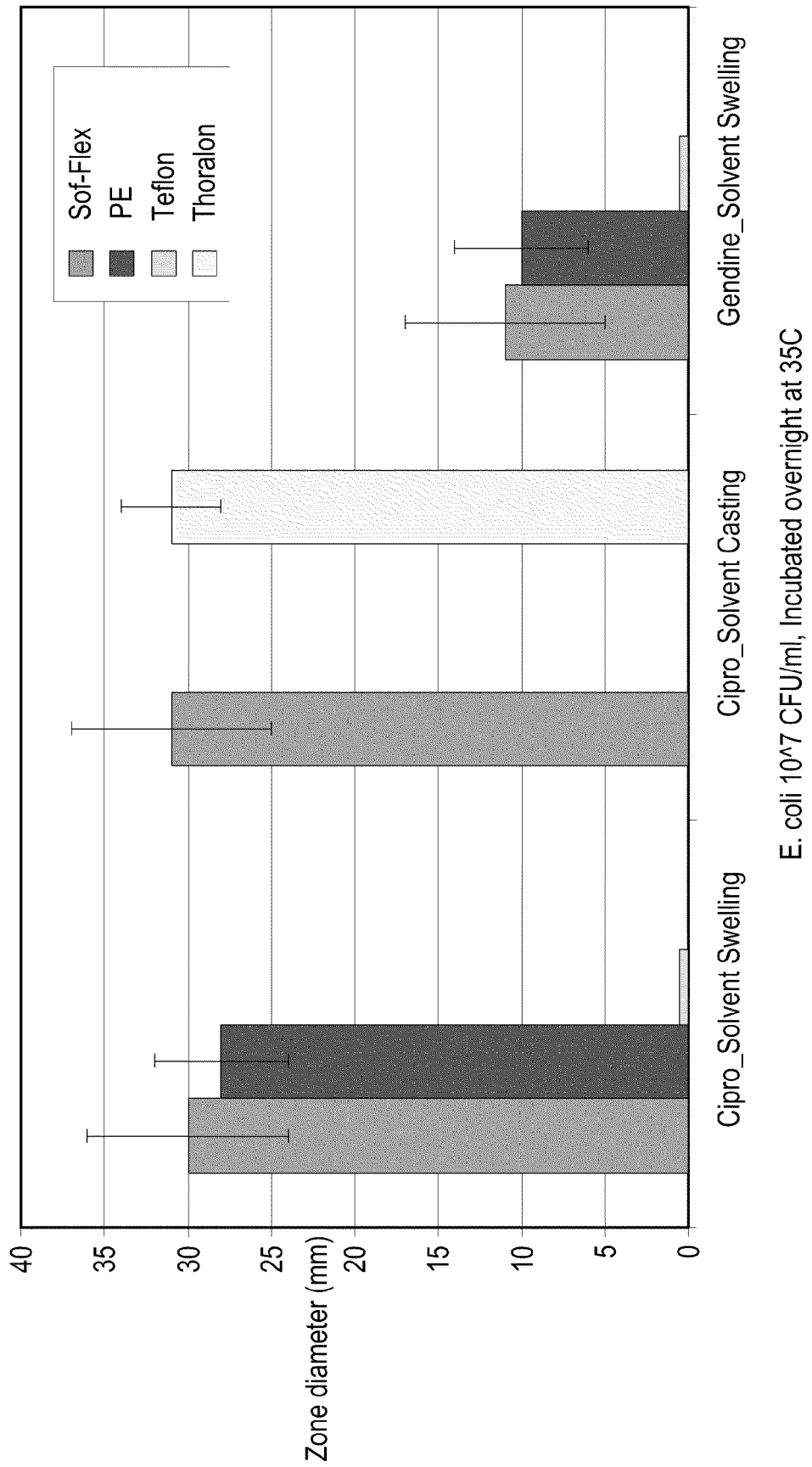

Testing with 10 times diluted bateria suspension (dropped from 10^8 CFU/ml to 10^7 CFU/ml), Graph 3 (FIG. 9) below shows similar information: (1) ciprofloxacin is very effective in inhibiting *E. coli*; and (2) coating methods (Solvent Swelling and Solvent Casting) used in this study are also advantageous in either polyurethane or polyethylene or Thoralon materials. However, those methods did not show desirability in Teflon material.

While the present invention has been described in terms of preferred embodiments, it will be understood, of course, that the invention is not limited thereto since modifications may be made to those skilled in the art, particularly in light of the foregoing teachings.

The invention claimed is:

1. An implantable drainage device for treatment of a stricture of a body vessel, the device comprising:
    a drainage tube including an inlet and extending to an outlet to define a drainage lumen formed through the inlet and outlet, the drainage tube including a swell layer and an outer polymeric layer formed about the swell layer, the outer polymeric layer defining a plurality of pores formed radially and exposing portions of the swell layer, the swell layer having an agent dispersed thereabout for regulated drug elution through the holes of the outer polymeric layer.

2. The device of claim 1 wherein the agent comprises at least one of an antimicrobial agent and an antithrombogenic agent.

3. The device of claim 1 wherein the agent is an antimicrobial agent comprising at least one of the following:
    cephaloporins, clindamycin, chlorampheanicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin and nikko Z.

4. The device of claim 3, further comprising an antithrombogenic agent dispersed in the swell layer, the antithrombogenic agent comprising at least one of the following: phosphorylcholine and heparin.

5. The device of claim 1 further comprising an anchoring component including an inlet array and an outlet array of radially extending flaps extending from the drainage tube to anchor the device within the body vessel.

6. The device of claim 5 wherein the inlet array is disposed proximate the inlet.

7. The device of claim 5 wherein the outlet array is disposed proximate the outlet of the drainage tube.

8. The device of claim 1, wherein the drainage tube has a pigtail shape.

9. An implantable drainage device for treatment of a stricture of a body vessel, the device comprising:
    a drainage tube including an inlet and outlet, the drainage tube including a swell layer and a cast layer formed about the swell layer having a first agent dispersed thereabout for regulated drug elution through the cast layer, the cast layer having a second agent disposed thereabout for drug elution therefrom; and
    an anti-reflux member cooperable with the outlet of the drainage tube, the anti-reflux membrane having an inlet bore and an outlet bore in fluid communication with the inlet bore, the inlet and outlet bores being in non-aligned relationship to reduce backflow from the outlet bore to the inlet bore of the anti-reflux member.

10. The device of claim 9 wherein the second agent comprises at least one of an antimicrobial agent and an antithrombogenic agent.

11. The device of claim 10 wherein the antimicrobial agent comprises at least one of the following: cephaloporins, clindamycin, chlorampheanicol, carbapenems, minocyclines, rifampin, penicillins, monobactams, quinolones, tetracycline, macrolides, sulfa antibiotics, trimethoprim, fusidic acid, aminoglycosides, amphotericin B, azoles, flucytosine, cilofungin and nikko Z.

12. The device of claim 10 wherein the antithrombogenic agent comprises at least one of the following: phosphorylcholine and heparin.

13. The device of claim 9 wherein the drainage tube comprises polymeric material including at least one of the following: elastomeric polyurethanes, polyurethane copolymers, silicones, polycarbonates, polyolefin, vinyl aromatic polymers, vinyl aromatic copolymers, ethylenic copolymers, polyacetals, chloropolymers, polyesters, polyester-ethers, polyamides, polyamide ethers, and polyethers.

14. The device of claim 9 further comprising a biodegradable coating layer disposed about the cast layer of the drainage tube for delayed drug elution of the second agent from the cast layer of the drainage tube.

15. The device of claim 14 wherein the biodegradable material comprises at least one of the following: polyesters, poly(amino acids), copoly(ether-esters), polyalkylenes oxalates, polyamides, poly(iminocarbonates), polyorthoesters, polyoxaesters, polyamidoesters, polyoxaesters containing amido groups, poly(anhydrides), polyphosphazenes, poly-alpha-hydroxy acids, trimethylene carbonate, poly-beta-hydroxy acids, polyorganophosphazines, polyanhydrides, polyesteramides, polyethylene oxide, polyester-ethers, polyphosphoester, polyphosphoester urethane, cyanoacrylates, poly(trimethylene carbonate), poly(iminocarbonate), polyalkylene oxalates, polyvinylpyrolidone, polyvinyl alcohol, poly-N-(2-hydroxypropyl)-methacrylamide, polyglycols, aliphatic polyesters, poly(orthoesters), poly(ester-amides), polyanhydrides, modified polysaccharides and modified proteins.

16. The device of claim 9, the anti-reflux member connecting an inlet tube portion and an outlet tube portion of the drainage tube, at least one of the inlet and outlet bores being located parallel to and offset from a central axis of the anti-reflux member.

* * * * *